(12) United States Patent
Musrock

(10) Patent No.: US 7,737,404 B2
(45) Date of Patent: Jun. 15, 2010

(54) SIGNAL ACQUISITION IN PET SCANNERS

(75) Inventor: Mark Musrock, Oak Ridge, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/034,107

(22) Filed: Feb. 20, 2008

(65) Prior Publication Data

US 2009/0072153 A1 Mar. 19, 2009

Related U.S. Application Data

(60) Provisional application No. 60/973,062, filed on Sep. 17, 2007.

(51) Int. Cl.
*G01T 1/164* (2006.01)

(52) U.S. Cl. .................................. 250/363.03

(58) Field of Classification Search ............ 250/363.02, 250/363.03, 363.04, 363.09, 369, 252.1
See application file for complete search history.

(56) References Cited

U.S. PATENT DOCUMENTS

| | | | | |
|---|---|---|---|---|
| 4,437,160 A | * | 3/1984 | Blum | 250/369 |
| 4,471,387 A | * | 9/1984 | Nadler | 358/497 |
| 5,677,536 A | * | 10/1997 | Vickers | 250/363.09 |
| 5,994,713 A | * | 11/1999 | Becker et al. | 250/591 |
| 6,232,604 B1 | * | 5/2001 | McDaniel et al. | 250/363.03 |
| 7,495,222 B2 | * | 2/2009 | Zhang et al. | 250/366 |
| 2001/0040219 A1 | * | 11/2001 | Cherry et al. | 250/363.03 |
| 2004/0232359 A1 | * | 11/2004 | Fiset | 250/504 R |

* cited by examiner

*Primary Examiner*—David P Porta
*Assistant Examiner*—Faye Bossalis
(74) *Attorney, Agent, or Firm*—Peter L. Kendall

(57) ABSTRACT

A Positron Emission Tomography (PET) scanner has a plurality of photo detector blocks. Each photo detector block or region has a plurality of photo detectors, a multiplexer receiving output signals from the plurality of photo detectors and generating a multiplexer output signal, a multiplexer control unit controlling switching of the multiplexer, and an analog-to-digital converter receiving the multiplexer output signal and generating a digital output signal.

26 Claims, 4 Drawing Sheets

SIGNAL ACQUISITION IN PET SCANNERS

CROSS-REFERENCE TO RELATED APPLICATIONS

This is a non-provisional patent application of pending U.S. provisional patent application Ser. No. 60/973,062, filed Sep. 16, 2007, by Mark Musrock, titled "Time Multiplexing PET Scintillation Block Photo Detector Signals Into a Single ADC", the entirety of which application is incorporated by reference herein.

TECHNICAL FIELD

The present invention concerns signal acquisition in Positron Emission Tomography (PET) scanners.

BACKGROUND

In the field of medical image technology such as Positron Emission Tomography (PET) or gamma cameras, as shown in FIG. 1, a plurality of scintillators 130 and associated photomultiplier tubes (PMTs) $110_n$ or avalanche photodiodes (APDs) are usually arranged in a circle of a detector ring 130. Such a detector ring 130 surrounds the patient to be scanned. To conduct a so-called PET scan, a short-lived radioactive tracer isotope, which decays by emitting a positron, is injected usually into the blood circulation of a living subject. After the metabolically active molecule becomes concentrated in tissues of interest, the research subject or patient is placed in the imaging scanner. The molecule most commonly used for this purpose is fluorodeoxyglucose (FDG), a sugar, for which the waiting period is typically an hour.

As the radioisotope undergoes positron emission decay, it emits a positron, the antimatter counterpart of an electron. After traveling up to a few millimeters the positron encounters and annihilates with an electron, producing a pair of gamma photons moving in almost opposite directions. These are detected when they reach one of a plurality of scintillation crystals in the scanning device, creating a burst of light detected by an array of photo detectors comprised either of photomultiplier tubes (PMTs) or silicon avalanche photodiodes (Si APDs). Generally a plurality of PMTs or APDs are arranged in a matrix and assigned to a single scintillator detector as shown in the enlarged section 160 in FIG. 1. The scintillator detector can be a single scintillation crystal or can be, as shown, a matrix of scintillator crystals 130 coupled to the PMTs via a light guide 135. To be able to increase the resolution of the system without the high costs of 1:1 coupling, the number of photo detectors per block is generally significantly lower than the number of scintillation crystals. For example, a block detector may have a plurality of photo detectors with, for example, 4 or 9 PMTs or APDs arranged in a 2×2 or 3×3 matrix behind an array of scintillation crystals. Other arrangements with more or less photo detectors are possible. Thus, the event localization may be determined or interpolated by such a scintillation block detector by processing the associated photo detector signals. This can be done by analog filtering, integration, and multiplication of weighted combinations of the photo detector signals or by using digital algorithms that use discrete time sample points of signals obtained directly from the photo detectors. The PET technique depends on simultaneous or coincident time detection of the pair of photons.

On the right side of FIG. 1a block diagram is shown of the typical architecture of detectors and associated analog-to-digital-converters in a conventional system. Each matrix of PMTs or APDs produces a plurality of signals that need to be processed to generate an image from a plurality of single events that are detected by a PMT. To determine the position of a detected annihilation, the system needs to accurately measure the timing and energy of both detected photons. Consequently a high amount of data has to be produced by the respective measurement circuits.

For example, as shown on the right side of FIG. 1, each scintillator has an associated matrix of detectors, such as PMTs $110_1 \ldots 110_n$. Each signal of each PMT $110_1 \ldots 110_n$ is first amplified, for example by an associated discriminator/filter $120_1 \ldots 120_n$ which are capable of optimizing desired photoelectron signal response while minimizing noise and amplifying the respective signals for further processing. The output signal of all discriminators/filters $120_1 \ldots 120_n$ are then concurrently converted into discrete-time digital signals by associated analog-to-digital converters (ADC) $140_1 \ldots 140_n$. The sample rate frequency for each ADC is provided at terminal 150. Using this digital processing architecture requires n independent ADC channels with peripheral circuitry to concurrently sample each of n photo detector signals per block. This causes high costs on the design of a detector unit.

SUMMARY

According to an embodiment, a Positron Emission Tomography (PET) scanner may comprise a plurality of photo detector blocks or panels, wherein each photo detector block or panel comprises a plurality of photo detectors; a multiplexer receiving output signals from said plurality of photo detectors and generating a multiplexer output signal; a multiplexer control unit controlling switching of said multiplexer; and an analog-to-digital converter receiving said multiplexer output signal and generating a digital output signal.

According to a further embodiment, the PET scanner may further comprise a plurality of discriminators/filters, wherein each discriminator/filter is coupled between an associated photo detector and said multiplexer. According to a further embodiment, a photo detector can be a photomultiplier tube (PMT) or an avalanche diode (APD). According to a further embodiment, each photo detector block may comprise four photo detectors. According to a further embodiment, the multiplexer can be a two-way multiplexer and each photo detector with discriminator/filter may generate a differential output signal. According to a further embodiment, the multiplexer can be a two-way multiplexer and may switch an associated signal and ground for each photo detector. According to a further embodiment, each block or panel may comprise a plurality of photo detectors divided into n groups, wherein each group comprises: m photo detectors; a multiplexer receiving output signals from said m detectors and generating a multiplexer output signal; a multiplexer control unit controlling switching of said multiplexer; and an analog-to-digital converter receiving said multiplexer output signal and generating a digital output signal.

According to another embodiment, a Positron Emission Tomography (PET) scanner may comprise a plurality of photo detector blocks or panels, wherein each photo detector block or panel comprises a plurality of photo detectors divided into n groups, wherein each group comprises m photo detectors; a multiplexer receiving output signals from said m detectors and generating a multiplexer output signal; a multiplexer control unit controlling switching of said multiplexer; and an analog-to-digital converter receiving said multiplexer output signal and generating a digital output signal.

According to a further embodiment, each group may comprise m discriminators/filter, wherein each discriminator/filter of said m discriminators/filter is coupled between an associated photo detector and said multiplexer. According to a further embodiment, a photo detector can be a photomultiplier tube (PMT) or an avalanche diode (APD). According to a further embodiment, each group may comprise three photo detectors. According to a further embodiment, the multiplexer can be a two-way multiplexer and each photo detector with discriminator/filter generates a differential output signal. According to a further embodiment, the multiplexer can be a two-way multiplexer and switches an associated signal and ground for each photo detector. According to a further embodiment, the multiplexer can be a two-way multiplexer and switches an associated signal for each photo detector.

According to another embodiment, a method of operating a Positron Emission Tomography (PET) scanner comprising a plurality of photo detector blocks or panels, wherein each photo detector block or panel comprises a single analog-to-digital converter, may comprise the steps of: for each photo detector block feeding a plurality of photo detectors signals to a multiplexer; multiplexing said photo detector signals to a single output signal; converting said single output signal by said analog-to-digital converter into a single digital output signal.

According to a further embodiment, the method may further comprise the step of discriminating/filtering each photo detector signal by an associated discriminator/filter. According to a further embodiment, the photo detector signal can be a signal from a photomultiplier tube (PMT) or an avalanche diode (APD). According to a further embodiment, each photo detector block may comprise four photo detectors. According to a further embodiment, the multiplexer can be a two-way multiplexer and each photo detector signal can be a differential output signal. According to a further embodiment, the multiplexer can be a two-way multiplexer and the step of multiplexing may comprise the step of switching a photo detector signal and an associated ground signal for each photo detector. According to a further embodiment, the multiplexer can be a two-way multiplexer and the step of multiplexing may comprise the step of switching a photo detector signal for each photo detector.

According to another embodiment, a method of operating a Positron Emission Tomography (PET) scanner comprising a plurality of photo detector blocks or panels, wherein each photo detector block or panel region comprises a plurality of photo detectors divided into n groups, wherein n>1, and each group comprises m photo detectors, wherein m>1, for each group the method may comprise the steps of: for each group feeding m photo detectors signals to a multiplexer; multiplexing said m photo detector signals to a single output signal; and converting said single output signal by said analog-to-digital converter into a single digital output signal.

According to a further embodiment, the method may further comprise the step of discriminating/filtering each photo detector signal by an associated discriminator/filter. According to a further embodiment, the multiplexer can be a m:1 multiplexer and the step of multiplexing may comprise the step of switching a fully differential output signal for each photo detector. According to a further embodiment, the multiplexer can be a m:1 multiplexer and the step of multiplexing may comprise the step of switching a photo detector signal and an associated ground signal for each photo detector. According to a further embodiment, the multiplexer can be a m:1 multiplexer and the step of multiplexing may comprise the step of switching only the photo detector signal for each photo detector.

BRIEF DESCRIPTION OF THE DRAWINGS

A more complete understanding of the present disclosure thereof may be acquired by referring to the following description taken in conjunction with the accompanying drawings wherein.

Figure 1:
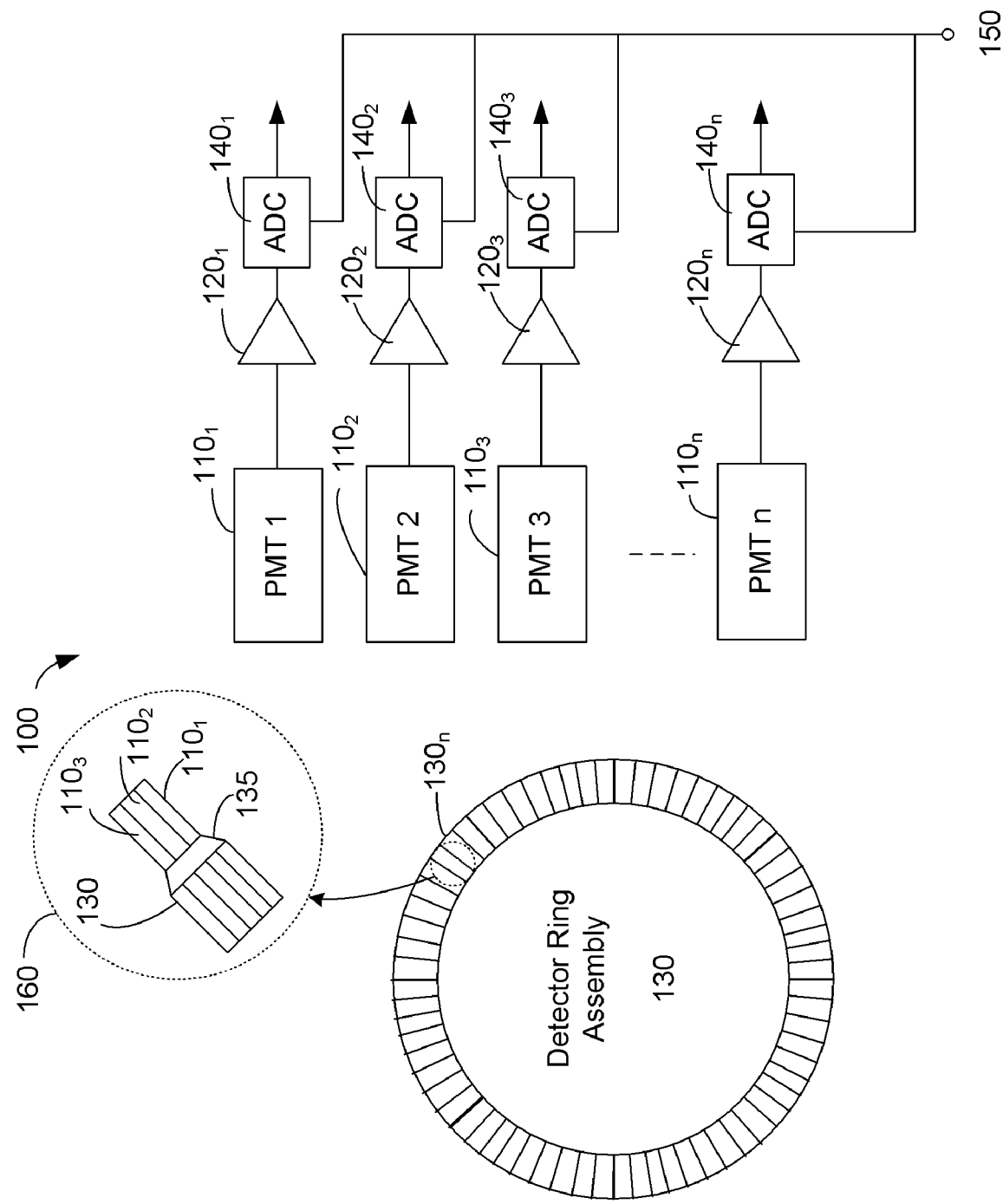
FIG. 1 shows a conventional detector ring assembly with associated detector circuitry of a conventional PET scanner.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

According to an embodiment, a low cost signal hardware architecture for use in a whole body PET scanner by time multiplexing photo detector signals associated with a detector block or panel into a single high speed analog-to-digital converter (ADC) can be accomplished. The current ADC sample rate $F_S$ for the energy and positioning channel of a whole body scanner is typically in the order of 50-100 Msps. According to an embodiment, the detector circuitry can, thus, be improved by reducing the channel costs significantly by time multiplexing at least some of the photo detector signals generated by photo detectors associated with a single scintillator crystal into a single high speed ADC channel. By appropriately shaping the position and energy signals, it is possible to time multiplex some or all of the photo detectors associated with a detector block or panel into a single high speed ADC with minimal loss in detector performance. Such an arrangement may be in particular beneficial in whole body PET scanners to reduce the overall electronic processing cost per channel.

In conventional systems, the current ADC sample rate $F_S$ for energy and positioning channel signals of a whole body scanner is typically in the order of 50-100 Msps. According to an embodiment, analog switch electronic components that have switching time specifications $t_{on}/t_{off}$ of less than 5 ns will enable multiple photo detector signals to be time multiplexed or time-shared into a single high speed ADC to reduce overall channel processing costs. This effectively results in a single ADC sampling rate frequency of 200 Msps. for a 4:1 multiplexing embodiment.

The cost savings depend on how many replicated ADC circuits can be substituted by a single ADC and associated switch circuitry, wherein the single ADC must comply with a respective higher sampling rate. However, some of the switching control logic can be advantageously integrated into existing field programmable gate arrays (FPGA) that are already used in conventional systems. Thus, only little additional hardware may be necessary. According to an embodiment, a two-pole switch may be used for each photo detector signal after appropriate differential analog filtering. However, according to another embodiment, single pole switches can be used with a reduced accuracy.

Figure 2:
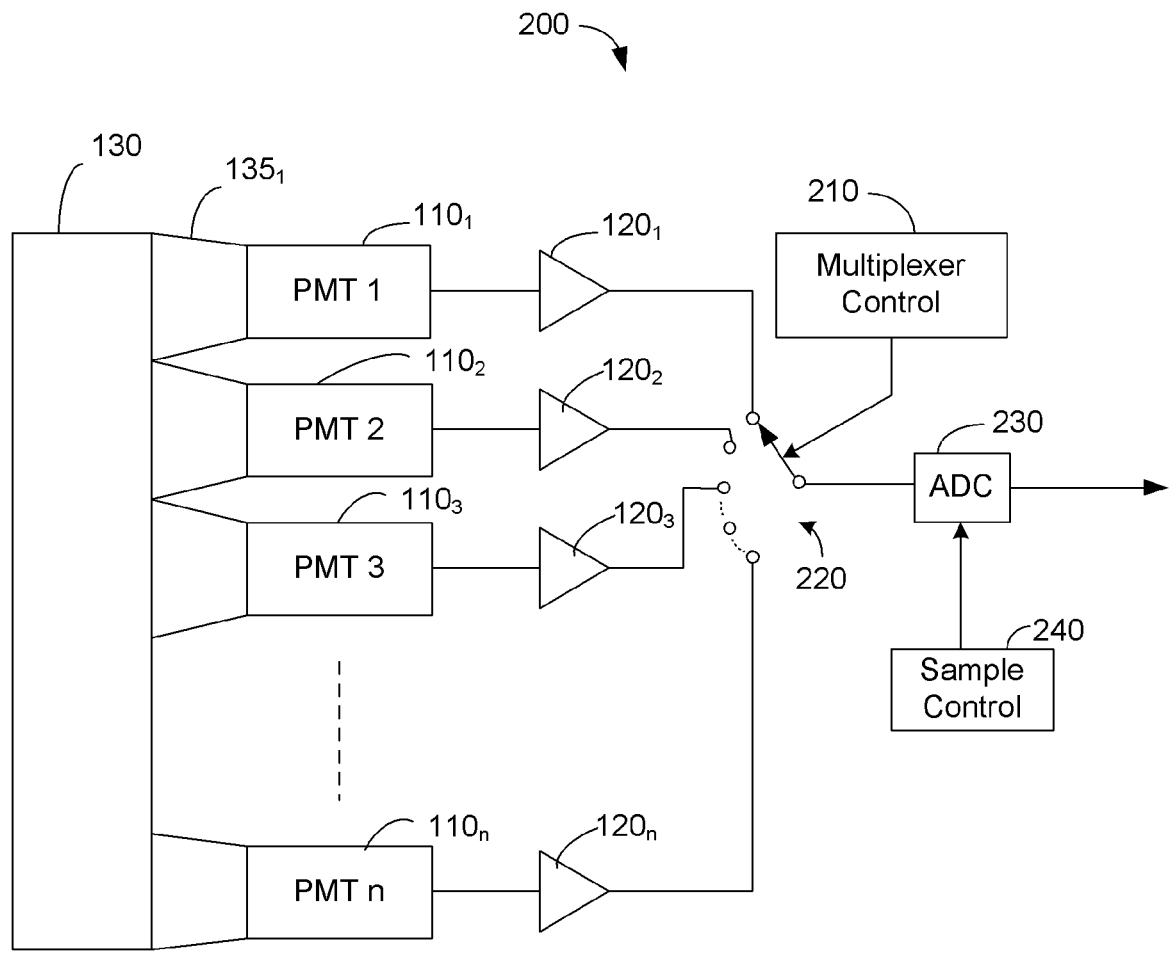
FIG. 2 shows circuitry associated with detector circuitry according to an embodiment.

FIG. 2 shows a first embodiment of a scintillator array 130 and associated n photo detectors, such as photomultiplier tubes (PMTs). However, the concept also applies to other photo detectors, such as avalanche photo diodes (APDs). The scintillator array 130 may be coupled with the PMTs via a plurality of light guides $135_n$. The present embodiments apply equally well to both a panel detector or a block detector design. A block detector physically breaks the detector area into a set of individual regions or blocks, each region containing a set of PMTs. In certain embodiments usually 4 PMTs are assigned to a region or block. However, other embodiments may use other assignment schemes. The PMTs are used to localize the photon event for this block region. The light emanating from any of the crystals in the block is localized to only this block region.

According to another embodiment, a panel detector design does not establish a physical block boundary between the individual detector regions and the lightguide is typically a sheet of glass. The light spreading from a scintillation crystal is not contained within the same "block region" as in a block design, but is allowed to spread. This ultimately leads to fewer PMTs per detector area than a block based design since it takes a smaller number of PMTs to localize the event. This type of detector design is also referenced as quadrant sharing in the literature.

The PMTs $110_1$, $110_2$, $110_3$, and $110_4$ each generate an output signal that is amplified, for example by an associated discriminator/filter $120_1 \ldots 120_n$. which are capable of minimizing noise and optimizing the photoelectron signal response and amplifying the respective signals for further processing. The output of each amplifier $120_1$, $120_2$, $120_3$, and $120_4$ is coupled with the input of an n:1 multiplexer 220. Multiplexer 220 is controlled by multiplexer control unit 210. The output of the n:1 multiplexer 220 is coupled with the input of high speed ADC 230. Appropriate sample and hold circuitry may be integrated into ADC 230. Sample control unit 240 provides for the sample clock $F_S$. At the output of ADC 230, a multiplexed detector digital photomultiplier signal stream is available.

Figure 3:
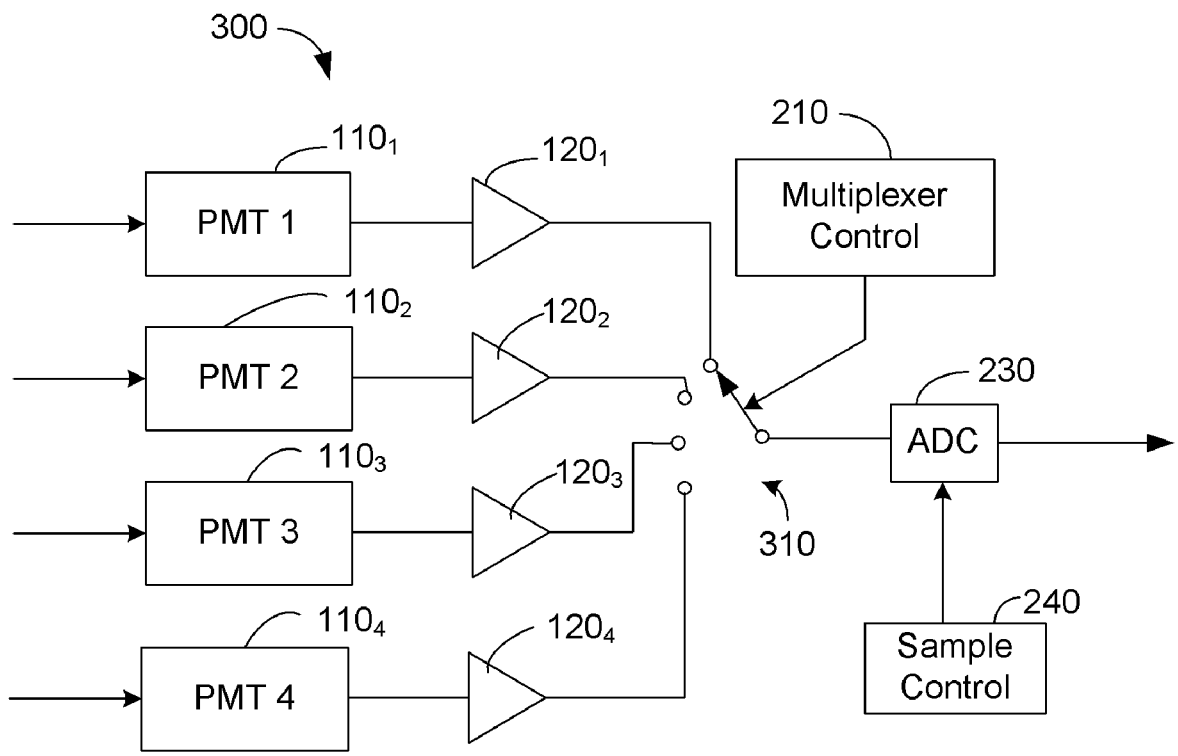
FIG. 3 shows an embodiment of single 2×2 detector matrix and associated detector circuitry.

According to an embodiment, each photoelectron signal from an associated photomultiplier is sampled at a sample rate of, for example, 50 Msps using an energy correction algorithm. Such an algorithm is for example disclosed in "Performance Characteristics of a New Generation of Processing Circuits for PET Applications", IEEE Trans. Nucl. Sci., Vol. 50, Issue 4, Part 1, pp. 974-978, August 2003, by Musrock, M. S., Young, J. W., Moyers, J. C., Breeding, J. E., Casey, M. E., Rochelle, J. M., Binkley, D. M., and Swann, B. K which is hereby incorporated by references. According to an embodiment, analog switches are used that enable a time multiplexing of, for example, four photo detector signals as shown in FIG. 3. To this end, multiplexer 310 has four inputs and an output. The output of the four PMTs $110_1$, $110_2$, $110_3$, and $110_4$ amplified by amplifiers $120_1$, $120_2$, $120_3$, and $120_4$ are fed to the four inputs of multiplexer 310 which is controlled by control unit 210. The output signal of multiplexer 310 is fed to high speed ADC 230 controlled by sample control unit 240. Thus, the photo detector signals from PMTs $110_1$, $110_2$, $110_3$, and $110_4$ are multiplexed into a single channel ADC signal every 20 ns. This effectively means that the single high speed ADC will be running asynchronously at n*50 Msps or in the case of FIG. 3 at 200 Msps for a 4:1 photo detector/block ratio.

Figure 4:
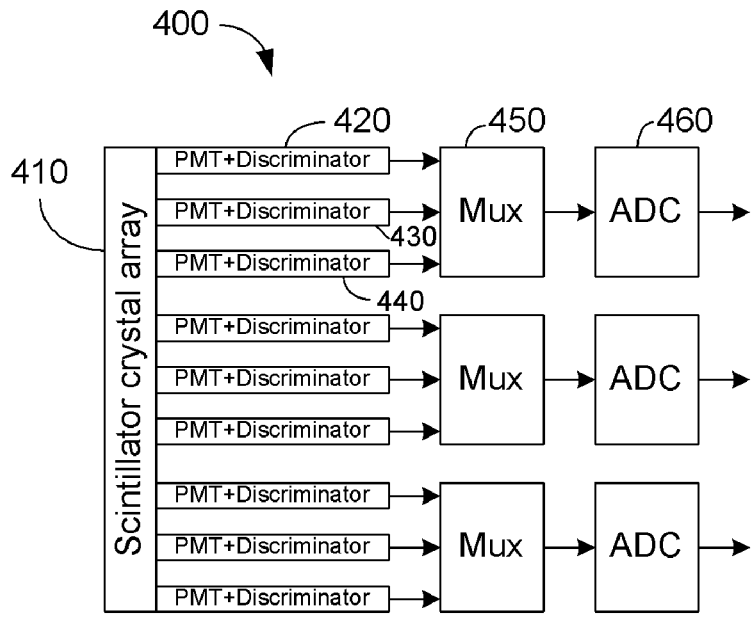
FIG. 4 shows an embodiment of single 3×3 detector matrix and associated detector circuitry.

FIG. 4 shows another example of a detector block having a 3×3 matrix of PMTs associated with a scintillator crystal array 410. The nine PMTs are grouped into three groups each having three PMTs and associated discriminators/filters 420, 430, and 440. The three output signals of each group 420, 430, 440 are fed to a multiplexer 450 whose single analog output signal is fed to high speed ADC 460 which produces the multiplexed digital photo detector stream. This embodiment, thus, generates three multiplexed digital photo detector signal streams for nine PMTs or APDs instead of nine discrete signals.

Figure 5:
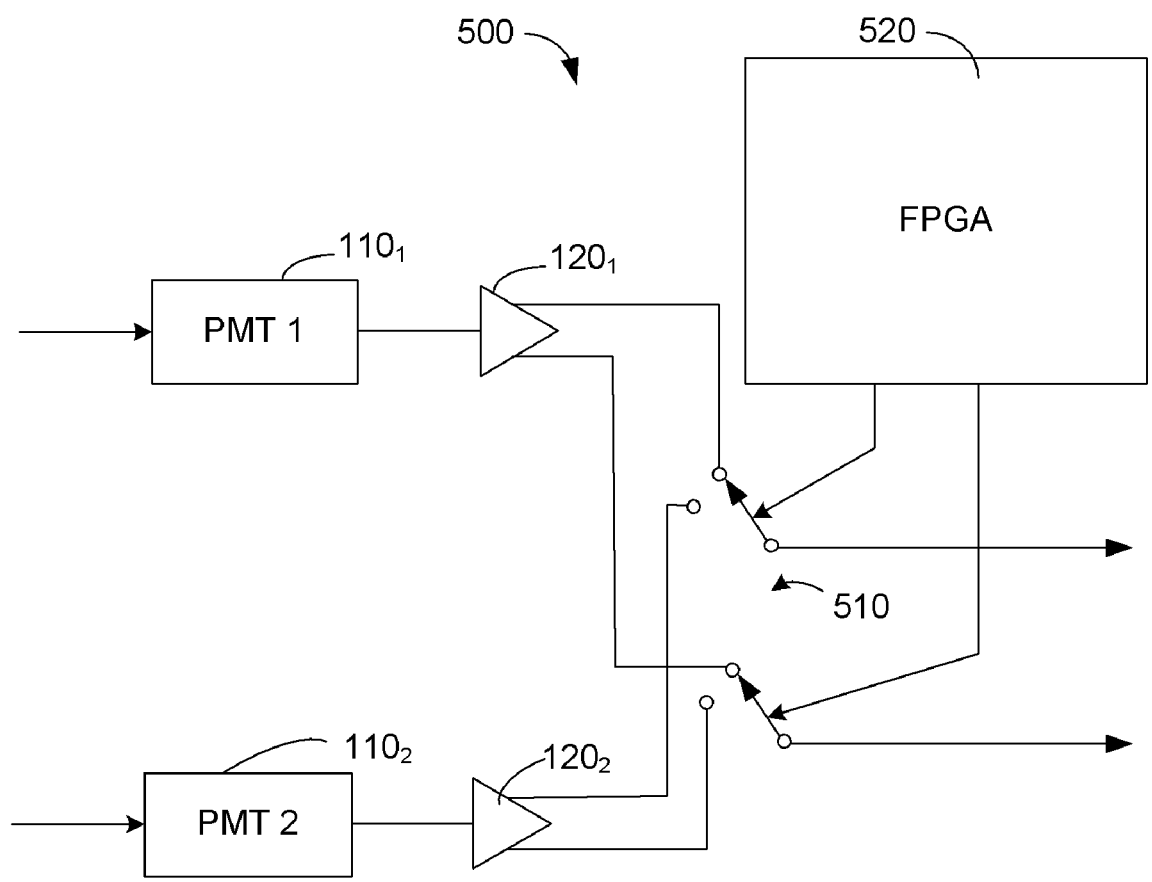
FIG. 5 shows an embodiment of a 2:1 multiplexer and associated control logic.

FIG. 5 shows an embodiment of a multiplexer capable of switching differential output signals or switching the main signal and associated ground for each PMT amplifier combination. In this embodiment, only two PMTs are shown. However, depending on the switching and conversion capabilities more than two photo detector signals may be multiplexed. The output signal of PMT $110_1$ is fed to amplifier $120_1$ which either generates a differential output signal or a non differential output signal. In case of a differential output signal, the fully differential signal is fed to the first input of the 2:1 multiplexer 510. In case of a non-differential signal, the signal and ground are fed to respective first inputs of the 2:1 multiplexer 510. Similarly the two outputs of a second PMT/amplifier combination $110_2$, $120_2$ are fed to the respective second inputs of the 2:1 multiplexer 510. According to another embodiment, the non-differential photo detector signals are 2:1 multiplexed wherein only the associated photo detectors signals without the associated signal grounds are multiplexed. FIG. 5 also shows an existing FPGA 520 wherein unused logic of FPGA 520 is programmed to provide for the respective control signals to control the switches of multiplexer 510 appropriately.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A Positron Emission Tomography (PET) scanner comprising a plurality of photo detector blocks or panels, wherein each photo detector block or panel comprises:
    a plurality of photo detectors;
    a two-way multiplexer receiving output signals from said plurality of photo detectors and generating a single time-shared multiplexer output signal;
    a multiplexer control unit controlling switching of said two-way multiplexer; and
    an analog-to-digital converter receiving said multiplexer output signal and generating a digital output signal.

2. The PET scanner according to claim 1, further comprising:
    a plurality of discriminators/filters,
    wherein each discriminator/filter is coupled between an associated photo detector and said two-way multiplexer.

3. The PET scanner according to claim 1, wherein a photo detector is a photomultiplier tube (PMT) or an avalanche diode (APD).

4. The PET scanner according to claim 1, wherein each photo detector block
    comprises four photo detectors.

5. The PET scanner according to claim 2, wherein each photo detector with discriminator/filter generates a differential output signal.

6. The PET scanner according to claim 1, wherein the two-way multiplexer switches an associated signal and ground for each photo detector.

7. The PET scanner according to claim 1, wherein each block or panel comprises a plurality of photo detectors divided into n groups, wherein each group comprises:
  m photo detectors;
  a two-way multiplexer receiving output signals from said m detectors and generating a multiplexer output signal;
  a multiplexer control unit controlling switching of said multiplexer; and
  an analog-to-digital converter receiving said multiplexer output signal and generating a digital output signal.

8. A Positron Emission Tomography (PET) scanner comprising a plurality of photo detector blocks or panels, wherein each photo detector block or panel comprises a plurality of photo detectors divided into n groups, wherein each group comprises:
  m photo detectors;
  a two way multiplexer receiving output signals from said detectors and generating a single time-shared multiplexer output signal;
  a multiplexer control unit controlling switching of said two-way multiplexer; and
  an analog-to-digital converter receiving said multiplexer output signal and generating a digital output signal.

9. The PET scanner according to claim 8, wherein each group comprising m discriminators/filter, wherein each discriminator/filter of said m discriminators/filter is coupled between an associated photo detector and said two-way multiplexer.

10. The PET scanner according to claim 8, wherein a photo detector is a photomultiplier tube (PMT) or an avalanche diode (APD).

11. The PET scanner according to claim 8, wherein each group comprises three photo detectors.

12. The PET scanner according to claim 8, wherein each photo detector with discriminator/filter generates a differential output signal.

13. The PET scanner according to claim 8, wherein the two-way multiplexer switches an associated signal and ground for each photo detector.

14. The PET scanner according to claim 8, wherein the two-way multiplexer switches an associated signal for each photo detector.

15. A method of operating a Positron Emission Tomography (PET) scanner comprising a plurality of photo detector blocks or panels, wherein each photo detector block or panel comprises a single analog-to-digital converter, the method comprising the steps of:
  for each photo detector block, feeding signals from a plurality of photo detectors to a two-way multiplexer;
  multiplexing said photo detector signals to a single time-shared output signal; and
  converting said single output signal by said analog-to-digital converter into a single digital output signal.

16. The method according to claim 15, further comprising the step of:
  discriminating/filtering each photo detector signal by an associated discriminator/filter.

17. The method according to claim 15, wherein the photo detector signal is a signal from a photomultiplier tube (PMT) or an avalanche diode (APD).

18. The method according to claim 15, wherein each photo detector block comprises four photo detectors.

19. The method according to claim 15, wherein each photo detector signal is a differential output signal.

20. The method according to claim 15, wherein the step of multiplexing comprises the step of:
  switching a photo detector signal and an associated ground signal for each photo detector.

21. The method according to claim 15, wherein the step of multiplexing comprises the step of:
  switching a photo detector signal for each photo detector.

22. A method of operating a Positron Emission Tomography (PET) scanner comprising a plurality of photo detector blocks or panels, wherein each photo detector block or panel region comprises a plurality of photo detectors divided into n groups, wherein n>1, and each group comprises m photo detectors, wherein m>1, for each group the method comprising the steps of:
  for each group feeding m photo detectors signals to a m:1 multiplexer;
  multiplexing said m photo detector signals to a single time-shared output signal; and
  converting said single output signal by said analog-to-digital converter into a single digital output signal.

23. The method according to claim 22, further comprising the step of discriminating/filtering each photo detector signal by an associated discriminator/filter.

24. The method according to claim 22, wherein the step of multiplexing comprises the step of:
  switching a fully differential output signal for each photo detector.

25. The method according to claim 22, wherein the step of multiplexing comprises the step of:
  switching a photo detector signal and an associated ground signal for each photo detector.

26. The method according to claim 22, wherein the step of multiplexing comprises the step of:
  switching only the photo detector signal for each photo detector.

* * * * *